United States Patent [19]

Theuwis et al.

[11] Patent Number: 4,566,343
[45] Date of Patent: Jan. 28, 1986

[54] SAMPLING AND/OR MEASURING APPARATUS FOR IMMERSION IN MOLTEN METAL

[75] Inventors: Alfons L. Theuwis, Zonhoven; Joseph M. Maes, Hechtel, both of Belgium

[73] Assignee: Electro-Nite Co., Philadelphia, Pa.

[21] Appl. No.: 611,788

[22] Filed: May 18, 1984

[30] Foreign Application Priority Data

Nov. 28, 1983 [BE] Belgium .............................. 2/60271

[51] Int. Cl.[4] .............................................. G01N 1/12
[52] U.S. Cl. ................................. 73/864.59; 73/432 R
[58] Field of Search .................... 73/432 B, 864.59; 374/139, 140; 136/234; 403/11, 23, 286

[56] References Cited

U.S. PATENT DOCUMENTS 4,015,475  4/1977  Pluschkell .................... 73/864.59
4,408,924 10/1983  Huebner ............................ 403/23
4,468,009  8/1984  Clauss ................................ 374/140

FOREIGN PATENT DOCUMENTS 2236966  7/1972  Fed. Rep. of Germany ...... 374/139

Primary Examiner—S. Clement Swisher
Attorney, Agent, or Firm—Seidel, Gonda, Goldhammer & Abbott

[57] ABSTRACT

Apparatus for immersion in molten metal includes a disposable probe telescoped over an immersion end of a lance up to a shoulder on the lance. An elastic ring seal is provided between the shoulder and the adjacent end portion of the probe for protecting the joint between the probe and the shoulder.

12 Claims, 15 Drawing Figures

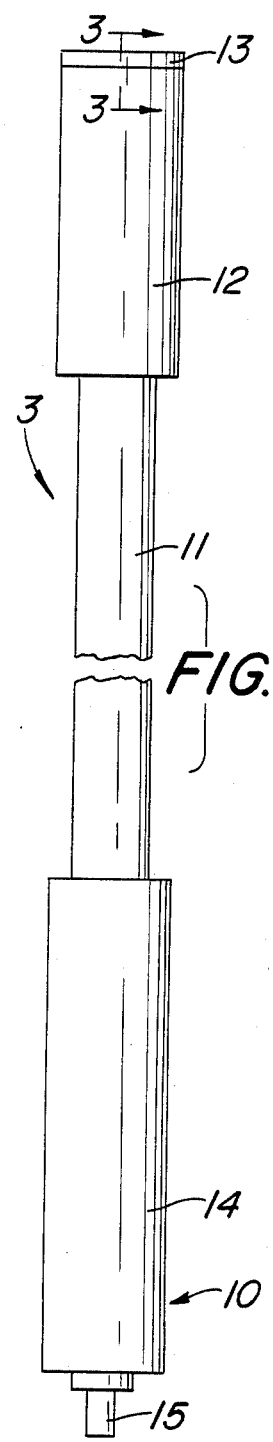
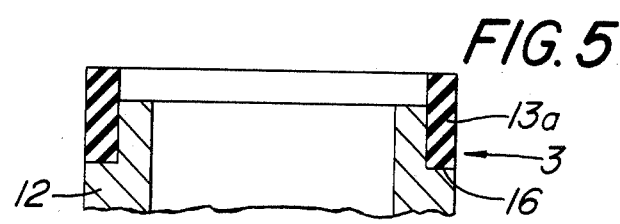
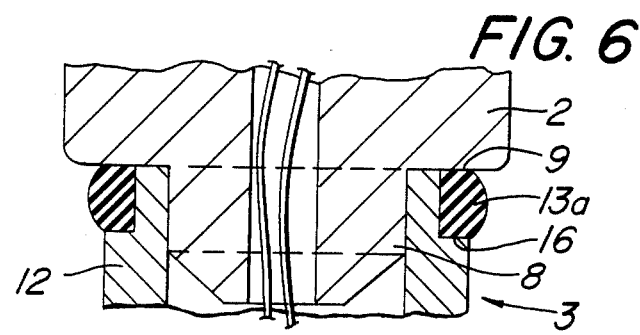
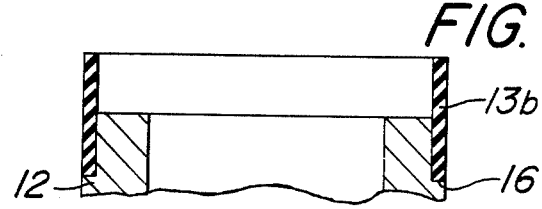
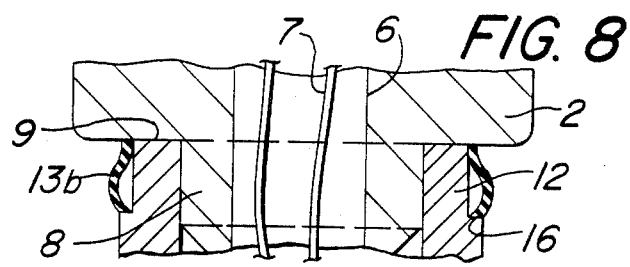
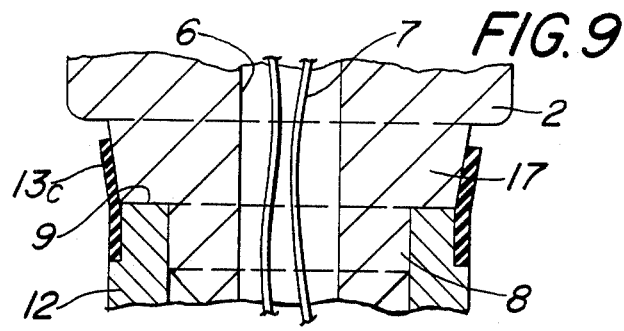

SAMPLING AND/OR MEASURING APPARATUS FOR IMMERSION IN MOLTEN METAL

BACKGROUND OF THE INVENTION

It is known to provide sampling and/or measuring apparatus for immersion in molten metal. The apparatus typically includes a lance on which it is removably mounted a disposable probe. A lance is typically made of metal whereas the disposable probe includes a tube of paperboard which is telescoped over an immersion end portion of the lance with a force fit until the end of the tube engages a shoulder on the lance. The probe at the end thereof remote from said shoulder typically supports a sampling chamber and/or one or more sensing elements.

The sensing elements supported by the disposable probe are electrically coupled to a connector on the tube. The connector on the tube is coupled to contacts on the lance. The contacts are coupled to recording instruments by way of wires which extend through the hollow lance. When the apparatus is used in connection with a converter, the probe is vertically immersed into the converter adjacent to the oxygen supply lance.

Apparatus in accordance with the present invention has considerable length and can be as long as 20 meters. It is necessary to take samples and/or measurements when the bath is under relatively calm circumstances as well as when the bath is turbulent such as during the oxygen blow. As a result of the length of the lance, and under turbulent circumstances, the lance vibrates. When the lance is immersed into the molten bath, liquid metal and slag will splash upwardly. It is possible for such splash to solidify and result in a deposit of frozen metal on the joint between the shoulder of the lance and the upper end of the probe tube. When a new probe is telescoped onto the lance, the frozen metal interferes with proper mating of the connector and contacts and also interferes with a good mechanical connection between the probe and the lance. As a result thereof, an improper reading may be obtained.

The present invention is directed to the solution of the problem of how to prevent the deposit of frozen metal at the joint between the probe and the lance.

SUMMARY OF THE INVENTION

The present invention is directed to apparatus for immersion in molten metal and includes a lance supporting a disposable probe. The probe is telescoped over an immersion end of the lance up to a shoulder on the lance. A means is provided for protecting the joint between the probe and the shoulder. Such means includes an elastic ring seal between the shoulder and the adjacent end portion of the probe. The seal is disposable after a single use.

It is an object of the present invention to provide immersion apparatus for measuring and/or sampling molten metal while minimizing the possibility of depositing frozen metal at the joint between the lance and probe.

Other objects will appear hereinafter.

For the purpose of illustrating the invention, there is shown in the drawings a form which is presently preferred; it being understood, however, that this invention is not limited to the precise arrangements and instrumentalities shown.

FIG. 2 is an elevation view of a probe forming part of the present invention.

FIG. 5 is a sectional view similar to FIG. 3 but showing an alternative embodiment of the seal.

FIG. 6 is a view similar to FIG. 4 but showing the alternative embodiment of FIG. 5.

FIG. 7 is a view similar to FIG. 3 but showing another alternative embodiment.

FIG. 8 is a view similar to FIG. 4 but showing the embodiment of FIG. 7.

FIG. 9 is a view similar to FIG. 4 but showing another embodiment

DETAILED DESCRIPTION

Figure 1:
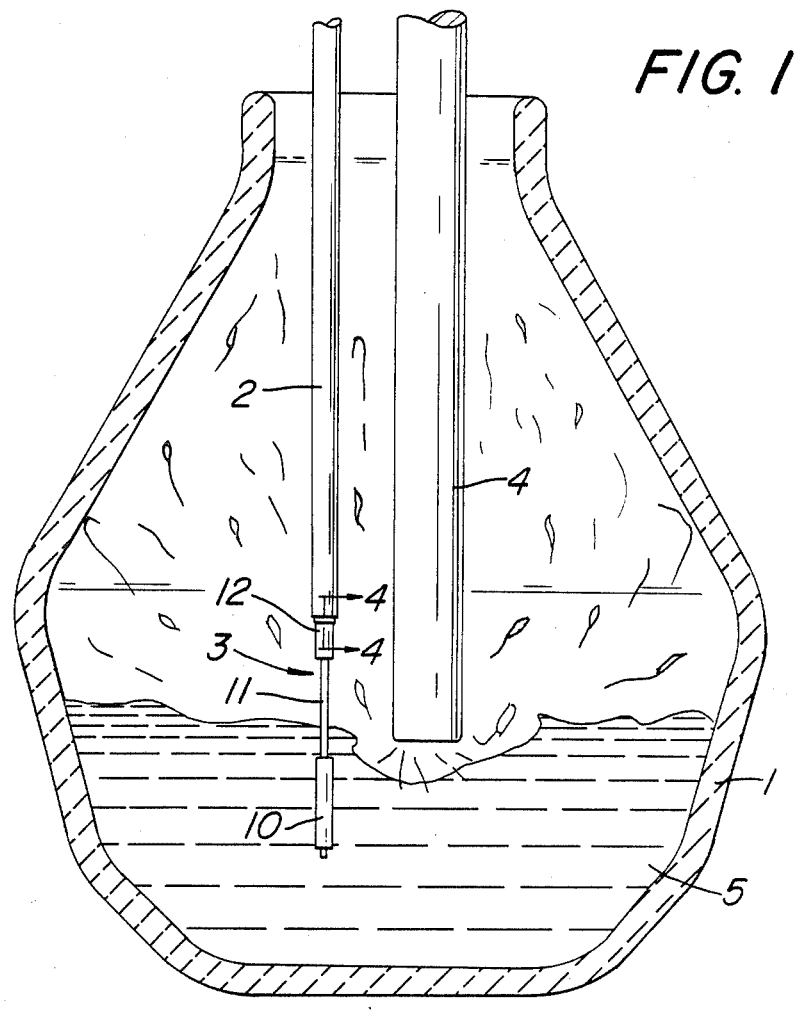
FIG. 1 is a diagrammatical representation of a cross section of a converter provided with apparatus in accordance with the present invention.

Referring to the drawing in detail, wherein like numerals indicate like elements, there is shown in FIG. 1 a converter 1 containing a bath of molten metal 5 such as molten steel. A lance 2 has a disposable probe 3 attached to one end thereof. The lance 2 is along side the oxygen lance 4.

The immersion lance 2 is a hollow metal tube having an internal cavity or bore 6 through which extends electrical conductors 7. The conductors 7 electrically couple a recording instrument with the probe 3. As shown more clearly in FIG. 4, the metal lance 2 has a tapered projection 8 at one end thereof so as to project from the stop shoulder 9.

The probe 3 includes a measurement and sampling portion 10 supported at one end of a disposable tube made from a material such as paperboard. Tube 11 is telescoped into and secured to a larger diameter tube 12 of material such as paperboard. A ring seal 13 made from an elastic polymeric plastic material is seated on the upper end of the tube 12. Except for ring seal 13, the construction of probe 3 is per se known. The portion 10 comprises a sampling chamber and/or one or more measuring cells such as a cell for measuring oxygen content of the bath, and/or a cell for measuring the temperature of the liquid bath 5 and may include a cell for measuring the temperature of the sample as it solidifies in the sampling chamber. A disposable cap 15 is preferably provided to protect the cell.

The probe 3 is made from tubes 11 and 12 having different diameters for convenience at the mechanized mounting on the lance. The inner diameter of tube 12 is chosen so as to have a slight force onto the projection 8 of the lance 2. The joint between the paperboard tube 12 and the metal lance 2 is the area to be protected in accordance with the present invention.

Figure 4:
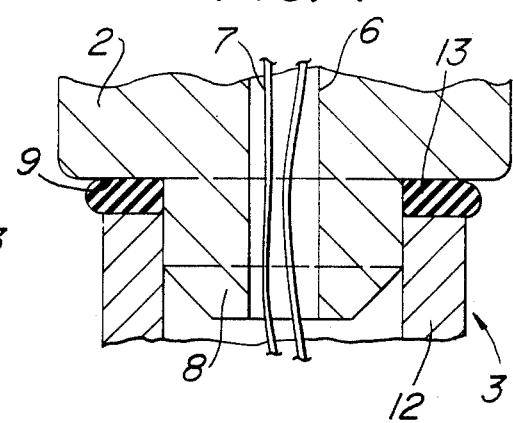
FIG. 4 is a sectional view taken along the line 4—4 in FIG. 1 but on an enlarged scale.

The ring seal 13 has an outer diameter corresponding to the outer diameter of tube 12. When projection 8 is telescoped into the tube 12, the shoulder 9 deforms the ring seal 13 as shown in FIG. 4. Ring seal 13 may be described as being an O-ring. The deformed ring seal 13 as shown in FIG. 4 protects the joint between the tube 12 and the lance 2. Ring seal 13 remains tight and protects the joint even during vibratory movement of the probe 3 relative to the lance 2. In practice, it is desirable that the ring seal 13 be able to compensate for changes in distance of at least 0.3 cm.

In addition to the above, the ring seal 13 should be sufficiently heat resistant and sufficiently inexpensive. A suitable material for the ring seal 13 is silicone rubber. Ring seal 13 is preferably a closed ring but may have free ends which overlap. The ring seal 13 is preferably attached to the end of the tube 12 in any convenient manner such as by use of glue or staples which do not interfere with the one time use of the ring seal 13. The ring seal 13 can have a diameter of 1 cm and is deformed by at least 50% when the probe 3 is telescoped onto the projection 8 of the lance 2. See FIG. 4.

Figure 3:
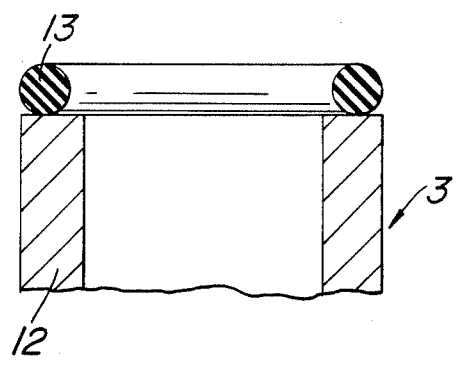
FIG. 3 is a sectional view taken along the line 3—3 in FIG. 2 but on an enlarged scale.

One disadvantage of the embodiment shown in FIGS. 3 and 4 is that the tube 12 does not make any direct contact with the shoulder 9 and therefore looses some of its stability. This disadvantage is rectified by the embodiments shown in FIGS. 5–15 wherein the upper end of the tube 12 is permitted to contact the stop shoulder 9.

As shown more clearly in FIG. 5, the ring seal 13a is rectangular in section and is in the form of a tube which projects beyond the upper end of the tube 12. The diameter of the tube 12 at the upper end thereof is reduced so as to provide a shoulder 16 on which the ring seal 13a rests. The diameter of ring seal 13a corresponds to the diameter of tube 12. When this embodiment is telescoped onto the projection 8 of the lance 2, as shown in FIG. 6, the upper end of the tube 12 contacts the shoulder 9 which also performs the function of deforming the ring seal 13a. Shoulders 9 and 16 are parallel and juxtaposed to one another.

In FIGS. 7 and 8 there is illustrated another embodiment of the present invention wherein the ring seal 13b rests on the shoulder 16 and projects above the upper end of the tube 12. Ring seal 13b is similar to ring seal 13a but the former is substantially thinner in its radial thickness. Also, exactly one half of the ring 13b is telescoped over the upper end of the tube 12. The embodiment of FIGS. 7 and 8 is otherwise the same as that shown in FIGS. 5 and 6.

In FIG. 9, there is illustrated another embodiment of the present invention wherein the ring seal 13c is similar to ring seal 13b. The outer diameter of the shoulder 9 corresponds to the outer diameter of the reduced portion at the upper end tube 12 so that the free end portion of the ring seal 13c may be stretched and tensioned over the conical portion 17 on the lance 2. Thus, the embodiment of the ring seal in FIG. 9 deforms by stretching rather than being deformed by compression.

Figure 10:
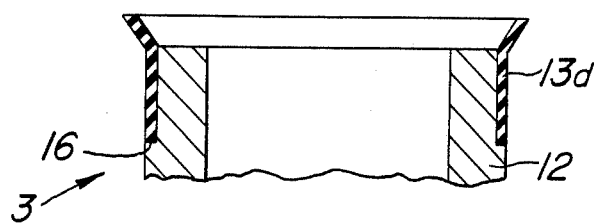
FIG. 10 is a view similar to FIG. 3 but showing another embodiment.
Figure 11:
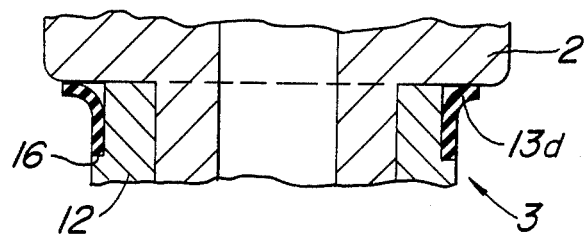
FIG. 11 is a view similar to FIG. 4 but showing the embodiment of FIG. 10.

In FIGS. 10 and 11 there is illustrated another embodiment of the present invention wherein the ring seal is designated 13d. Ring seal 13d is similar to ring seal 13c except that the portion which projects beyond the upper end of tube 12 is preformed so as to be tapered. When the lance 2 is telescoped into the tube 12 as shown in FIG. 11, the ring seal 13 will bend outwardly at the upper end thereof upon contact with the shoulder 9 as shown more clearly in FIG. 11.

Figure 12:
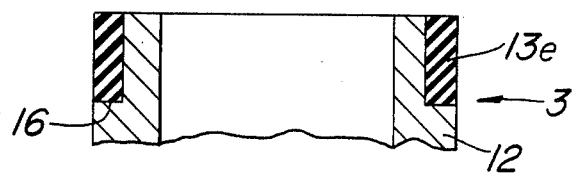
FIG. 12 is a view similar to FIG. 3 but showing another embodiment.
Figure 13:
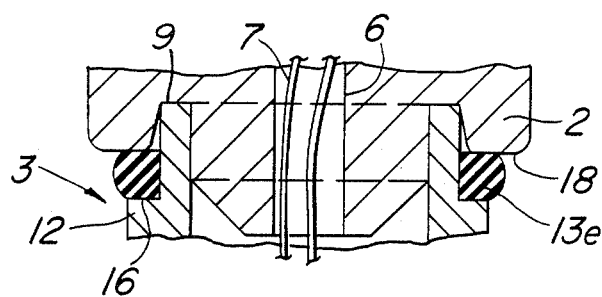
FIG. 13 is a view similar to FIG. 4 but showing the embodiment of FIG. 12.

In FIG. 12, there is illustrated another embodiment of the present invention wherein the ring seal is designated 13e. Ring seal 13e rests on the shoulder 16 on the tube 12 but does not project beyond the upper end of the tube 12. When the probe 3 is mounted on the lance 2, the ring 13e is deformed between shoulder 16 and the shoulder 18 which surrounds shoulder 9 on the lance 2.

Figure 14:
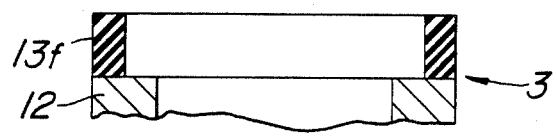
FIG. 14 is a view similar to FIG. 3 but showing another embodiment.
Figure 15:
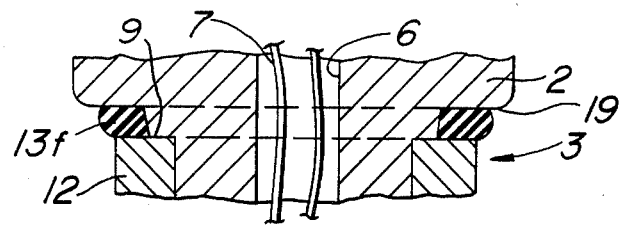
FIG. 15 is a view similar to FIG. 4 but showing the embodiment of FIG. 14.

In FIGS. 14 and 15, there is illustrated another embodiment of the present invention wherein the ring seal is designated 13f. Ring seal 13f is mounted on the upper end of the tube 12 in the same manner as ring seal 13. The ring seal 13f is rectangular in cross section and has an outer diameter corresponding to the outer diameter of the tube 12. When the probe 3 is telescoped onto the lance 2, the ring seal 13f is deformed as a result of contact with the end face of the tube 12 and the shoulder 19 on lance 2.

In each of the embodiments disclosed herein, the elastic ring seal is provided in a manner so that it may be deformed by contact with a shoulder on the lance 2. In each embodiment, the outer diameter of the ring seal is the same as the outer diameter of the tube 12. In connection with FIGS. 5–15, the ring seal is tubular and rectangular in section.

The present invention may be embodied in other specific forms without departing from the spirit or essential attributes thereof and, accordingly, reference should be made to the appended claims, rather than to the foregoing specification, as indicating the scope of the invention.

We claim:

1. Apparatus for immersion into molten metal comprising a lance supporting a disposable probe, said probe being telescoped over an immersion end of said lance, said lance having a shoulder adjacent one end of said probe, means for protecting the shoulder while permitting contact between said probe and shoulder, said means including an elastic ring seal between said shoulder and an adjacent end portion of said probe, said seal being disposable after a single use.

2. Apparatus in accordance with claim 1 wherein the outer diameter of said ring seal is substantially equal to the outer diameter of said probe.

3. Apparatus in accordance with claim 1 wherein said ring seal is tubular and rectangular in section.

4. Apparatus in accordance with claim 1 wherein said ring seal overlies a portion of the outer periphery of said probe adjacent said probe end.

5. Apparatus in accordance with claim 1 wherein said ring seal projects beyond the probe end prior to being deformed by contact with said shoulder.

6. Apparatus in accordance with claim 1 wherein said probe has a shoulder adjacent said tube end, one end of said ring seal being in contact with the last mentioned shoulder, the other end of said ring seal being in contact with the shoulder of said lance.

7. Apparatus in accordance with claim 1 wherein said seal is disposed between an end face of said probe and said shoulder on said lance.

8. Apparatus in accordance with claim 1 wherein an end face of said probe is in contact with said shoulder on said lance, said ring seal surrounding the interface between said probe and shoulder.

9. Apparatus for immersion in molten metal comprising a disposable probe adapted to be telescoped over an immersion end of lance, means on one end of said probe for protecting said probe end and a portion of a lance adjacent said probe end when said probe is telescoped over the immersion end of the lance, said means including an elastic ring seal which is disposable after a single use, the outer diameter of said ring seal being substantially equal to the outer diameter of said probe.

10. Apparatus in accordance with claim 9 wherein said ring seal is tubular and has an axial length which is greater than its radial thickness.

11. Apparatus in accordance with claim 10 including a reduced diameter portion on said one end of said probe so as to define a shoulder on the probe, one end of said ring seal being in contact with said shoulder.

12. Apparatus in accordance with claim 10 wherein said ring seal projects beyond said one end of said probe.

* * * * *